United States Patent [19]
LaFuente

[11] Patent Number: 5,893,872
[45] Date of Patent: Apr. 13, 1999

[54] METHOD OF ENHANCING THE APPEARANCE OF A BODY AREA AND FOR MANUFACTURING A MASK FOR USE IN SUCH METHOD

[75] Inventor: Henry LaFuente, Edmond, Okla.

[73] Assignee: IFS, L.C., Oklahoma City, Okla.

[21] Appl. No.: 08/775,716

[22] Filed: Dec. 17, 1996

Related U.S. Application Data

[60] Provisional application No. 60/008,787, Dec. 18, 1995.

[51] Int. Cl.$^6$ ............................................. A61F 13/12
[52] U.S. Cl. .................................. 606/204.35; 602/74
[58] Field of Search ........................ 606/201, 204.15, 606/204.35; 602/8, 74

[56] References Cited

U.S. PATENT DOCUMENTS

| D. 113,429 | 2/1939 | Mehl . |
|---|---|---|
| 165,955 | 7/1875 | Rowley . |
| 891,653 | 6/1908 | Von Alpenburg . |
| 1,099,967 | 6/1914 | Cochrane . |
| 1,110,772 | 9/1914 | Gunderman . |
| 1,113,732 | 10/1914 | Archibald . |
| 1,247,222 | 11/1917 | Cauffman . |
| 1,693,452 | 11/1928 | McCune . |
| 1,810,486 | 6/1931 | Lancaster . |
| 1,938,554 | 12/1933 | Ager . |
| 2,477,883 | 12/1949 | Lefohn . |
| 2,671,446 | 3/1954 | Mann . |
| 2,923,291 | 2/1960 | Lagoma . |
| 3,529,601 | 9/1970 | Kirkland . |
| 3,805,782 | 4/1974 | Welch . |
| 4,117,837 | 10/1978 | Remiro . |
| 4,247,351 | 1/1981 | Rechenberg . |
| 4,735,754 | 4/1988 | Buckner . |
| 4,809,690 | 3/1989 | Bouyssi et al. . |
| 5,277,700 | 1/1994 | Smith . |

FOREIGN PATENT DOCUMENTS

| 0 063 875 | 11/1982 | European Pat. Off. . |
|---|---|---|
| 0 288 741 | 11/1988 | European Pat. Off. . |
| 1334461 | 6/1962 | France . |

*Primary Examiner*—Michael Buiz
*Assistant Examiner*—William W. Lewis
*Attorney, Agent, or Firm*—Gary Peterson

[57] ABSTRACT

A method of enhancing the appearance of a body area having wrinkles, blemishes or excess mass or having been disfigured by an injury such as a burn. A cosmetic mask having a specially sculpted body contacting surface adapted to treat a subject's distinctive bodily characteristics is formed by first forming a negative impression of the subject's targeted body area; filling the impression with a hardening material; when the hardening material has hardened, separating the impression from the hardening material, the hardening material being in the form of a mold reflecting a positive image of the body area; sculpting the mold to achieve a desired body contacting surface; and forming a mask from the mold. After the mask is formed it is applied to the body area for a time sufficient to enhance the appearance of the body area.

22 Claims, No Drawings

METHOD OF ENHANCING THE APPEARANCE OF A BODY AREA AND FOR MANUFACTURING A MASK FOR USE IN SUCH METHOD

CROSS REFERENCE TO RELATED APPLICATION

This application claims the benefit of U.S. provisional application Ser. No. 60/008,787, filed Dec. 18, 1995 now abandoned.

BACKGROUND OF THE INVENTION

1. Technical Field

This invention relates generally to a method of enhancing the appearance of a body area having wrinkles, blemishes or excess mass or having been disfigured by an injury such as a burn. The invention encompasses a method of manufacturing a cosmetic mask having a specially sculpted body contacting surface adapted to treat a subject's distinctive bodily characteristics and the use of such a mask in connection with enhancing the appearance of such a body area.

2. Background

As a person ages, the skin, especially about the face and neck, loses the ability to respond as it once did and is prone to wrinkle, droop or otherwise lose its tautness. This condition may be exacerbated over time by sun exposure. Unwanted mass also may appear due to changes in metabolism and weight gain. These changes sometimes cause the person to feel inadequate or unattractive. In addition, injuries, especially burns, can cause unsightly disfigurations.

A variety of masks have heretofore been proposed for use on the body, particularly the face, to achieve a number of objectives, medical and cosmetic, examples of which are disclosed in the following United States patents:

(i) U.S. Pat. No. D113,429, issued to L. Mehl on Feb. 12, 1939, discloses a beauty mask. The mask extends down about the neck, and has ties.

(ii) U.S. Pat. No. 165,955, issued to H. Rowley on Jul. 27, 1875, shows a mask for medical purposes. The mask is a flexible rubber mask and permits medical preparations to be held on the skin underlying the mask.

(iii) U.S. Pat. No. 891,653, issued to V. Von Alperburg on Jun. 23, 1908, discloses a skin preserving covering. The covering has three layers, the inner trio comprising material from a Chinese palm tree, the outer layer comprising a reinforced textile layer. The intermediate layer has a "medicament" for preserving skin.

(iv) U.S. Pat. No. 1,099,967, issued to A. Cochrane on Jun. 16, 1914 shows a combined chin truss and ear compress.

(v) U.S. Pat. No. 1,110,772 issued to M. Gunderman on Sep. 15, 1914, discloses an appliance for removing facial defects. The appliance has a forehead band and a chin supporter.

(vi) U.S. Pat. No. 1,113,732 issued to C. Archibald on Oct. 13, 1914, shows a facial supporter. The supporter is made from a non-yielding material.

(vii) U.S. Pat. No. 1,247,222 issued to Z. Cauffman on Nov. 20, 1917, discloses a chin supporter. The supporter is made from a loosely woven textile material.

(viii) U.S. Pat. No. 1,693,452 issued to C. McCune on Nov. 27, 1928, shows a mask for facial treatments. The mask is made from silk.

(ix) U.S. Pat. No. 1,810,486 issued to R. Lancaster on Jun. 16, 1931, discloses a rubber mask. The mask is said to be useful in face reducing, complexion bleaching, and treatment of skin blemishes.

(x) U.S. Pat. No. 1,938,554 issued to G. Ager on Dec. 5, 1933, shows a face lifting and treating method and device. This device and method are intended to draw different parts of the face to their original status.

(xi) U.S. Pat. No. 2,671,446 issued to A. Mann on Mar. 9, 1954 discloses a beauty mask. The mask is worn for the eradication of wrinkles, for reshaping facial muscles, and for general treatment and improvement of the skin as by removal of blemishes. The mask includes a liner, and before use facial creams, lotions, and the like are applied to the skin-contacting face of the liner.

(xii) U.S. Pat. No. 2,923,291 issued to T. Lagoma on Feb. 2, 1960, shows a mask. The mask is used to correct wrinkles and other facial disfigurations.

(xiii) U.S. Pat. No. 3,529,601 issued to J. Kirkland on Sep. 22, 1970, discloses a therapeutic bandage. The bandage is an elastic material impermeable to air, and the bandage is wrapped about a portion of the body. The bandage is used for weight reduction.

(xiv) U.S. Pat. No. 3,805,782 issued to W. Welch on Apr. 23, 1974, shows a protective beauty mask. The mask protects facial skin and muscle tissue from pressure and distortion during sleep.

(xv) U.S. Pat. No. 4,117,837 issued to M. Emiro on Oct. 3, 1978, discloses a monopiece face mask for beauty treatment. The mask is formed from a stretchable material and covers the head.

(xvi) U.S. Pat. No. 4,809,690 issued to Bouyssi et al. on Mar. 7, 1989, shows a protective skull cap for the skull. The cap is formed from first talking an impression of the skull, and then layering three layers of non-flexible material over the impression to form the skull cap.

(xvii) U.S. Pat. No. 5,277,700 issued to V. Smith on Jan. 11, 1994, discloses a facial bandage. The facial bandage is used as a dressing for compression and/or support of facial features for medical treatment.

None of the above described patents, however, offers a method of manufacturing a cosmetic mask having a specially sculpted body contacting surface adapted to treat a subject's distinctive bodily characteristics.

It is thus an object of the invention to provide a method of making a cosmetic mask, including a facial mask, that allows for the accurate manufacture of a personalized, specially sculpted mask which will reduce wrinkles, blemishes and unwanted mass as desired.

Additionally, it is an object of the invention to provide a mask to effect cosmetic benefits to damaged body parts of victims of injury, such as burn victims. The invention may be utilized for various body parts, including a victim's back, chest, and appendages.

SUMMARY OF THE INVENTION

These and other objects are achieved through the use of a cosmetic mask having a specially sculpted body contacting surface adapted to treat a subject's distinctive bodily characteristics. The mask is made by first forming a negative impression of the subject's targeted body area. The impression is then filled with a hardening material. When the hardening material has hardened, the impression is separated from the hardening material to obtain a mold reflecting a positive image of the body area. The mold is sculpted to achieve a desired body contacting surface, and from the sculpted mold the mask is formed. After the mask is formed it is applied to the body area for a time sufficient to enhance the appearance of the body area.

Throughout this specification for purposes of illustration a facial mask embodiment is used as an example. It should be understood that while the ensuing description is directed primarily to the manufacture and use of a facial mask, as the facial mask is anticipated to be the widest application of the present invention, the invention is not so limited. The principles and methods disclosed are equally applicable to the manufacture and use of cosmetic masks for other body areas, including those areas damaged, scarred or disfigured through injury. Accordingly, references hereinbelow to the making and using of a facial mask should be taken to be equally applicable to the making and using of masks for other body areas.

Thus, in accordance with one aspect of the invention, the individual's face is cleaned in preparation for the masking process. A lab coat is placed over the individual and a disposable surgical hat is placed over the hair and tied into place. The individual is placed in a reclining chair and reclined to a 40 to 45 degree angle.

The entire face is covered with an alginate impression material from ⅛ inch to ¼ inch thick. Simultaneous to covering the face with the alginate impression material, small strips of gauze are applied to the soft alginate mixture. The strips are exposed above the surface of the alginate material.

With the gauze in place and the alginate impression material hardened, the alginate impression is covered with a plaster material. Before the plaster hardens, a wetted bandage wrap is used to cover the entire plastered area. This bandage wrap provides added strength to the plaster and protection to the alginate impression material during removal of the impression from the face. After the plaster has hardened, the plastered alginate impression is removed from the face. The alginate impression comprises a negative image of the individual's face.

The next step is to make a positive image from the negative image. The positive image is made by filling the negative image with a hardening material, such as plaster. The hardening material is of a consistency such that it will run into the many lines, wrinkles and other areas that require entry by a fairly liquid matter. It is assured that the plaster fills every wrinkle, crevice and indentation in the alginate impression. When hardened, the plastered alginate impression is removed to obtain a plaster mold comprising a positive image of the face. This positive image eventually will serve as a mold for the preparation of a plastic mask.

The plaster mold is sculpted and smoothed to eliminate the wrinkles, crevices, and other problem areas exposed thereon in accordance with the individual's requests. A plastic mask is then formed from the mold. A plastic sheet is heated, placed over the mold, and carefully pulled thereover as a second skin. The plastic is allowed to cool and is then removed. The edges, eye areas, mouth and nostrils of the mask are cut-out, rounded off and smoothed for comfortable fit. The prepared mask is double checked for fit against the mold.

The mask is then properly fitted to the individual. Once proper fit is achieved, straps are put on the mask to hold it in place while it is worn. Proper fit is maintained through readjustments to the mask. These readjustments are made by reheating the plastic mask and manipulating the contour of the mask to make appropriate changes.

The mask works to give support and pressure to troubled areas and may result in reducing the appearance of wrinkles, other blemishes caused by aged skin, and unwanted mass in the face.

As mentioned above, in accordance with another aspect of the invention a mask may be formed for other parts of the body, such as the back, chest, arms and legs of an individual. The same principles and methods may be used for forming body masks. Utilized as a cosmetic treatment for individuals sustaining any type of scarring or skin irregularity, including disfigurations caused by burns, a more normal appearance of the affected area can be achieved.

Still other objects and advantages of the present invention will become readily apparent to those skilled in this art from the following detailed description, wherein there is shown and described only the preferred embodiment of the invention, simply by way of illustration of the best mode contemplated for carrying out the invention. As will be realized, the invention is capable of modifications in various obvious respects, all without departing from the invention. Accordingly, the description should be regarded as illustrative in nature, and not as restrictive.

DETAILED DESCRIPTION OF THE PREFERRED EMBODIMENT

Preparation

The lab used to mask the individual should have a reclining chair, and access to both hot and cold running water. The first step is to prepare the individual by cleaning the face or other body area, removing all makeup and other material from the face or area. This is accomplished by using a sterile eyelid cleanser, such as a pre-moistened eyelid cleansing pad of a non-irritating, hypo-allergenic. The preferred cleaning pad comprises purified water USP, PEG-200 glyceryl tallowate, disodium laureth sulfosuccinate, cocamdopropytamine oxide, PEG-78 glyceryl cocoate, benzyl alcohol and edetate disodium. The preferred "brand" name is EYE SCRUB from Ciba Vision.

Once the face or other body area is clean, a lab coat is placed over the person covering the clothing worn, and a disposable surgical hat is placed over the hair and tied into place. Masking tape may be used to secure the hat in place and also to cover any hair not covered by the hat. When practicing the facial mask embodiment of the invention, the individual is placed in a "dental-type" chair and reclined to a 40 to 45 degree angle. Once the individual is comfortable and assured of safety, the physical masking process begins.

Making The Impression

A number of impression materials can be used. To this point, however, the preferred material is Alginate Impression Material-Type 1-Fast Set. The fast set is used because of the quality of the material and its ability to set fast and speed up the process.

A seven (7) gram scoop is used for measuring the alginate, which is in a powder form. Three (3) scoops of powder (21 g) are put in a plastic mixing bowl, along with one third measure (20 ml) of water at approximately 72° F. (22° C.). Colder water retards setting, while warmer water hastens setting. This mixture is spatulated for forty-five (45) seconds to produce a smooth creamy mix. Once the mix is ready to use, it is applied with a stainless steel spatula. The spatula should be about one (1) inch wide to assure control. When practicing the facial mask embodiment of the invention, the process begins with the neck area. The alginate mixture is spread in an upward motion, moving up the neck and around the chin and lower jaws area. The second area of coverage is around the mouth area and over the nose. The mouth and nose areas require special attention. It is necessary for the mouth to be closed, then covered completely. Working across the upper lip area, the nose is then covered with the nostrils open for breathing. The bridge of the nose is important because it will require strength when removed; therefore, it is important that this area is covered completely, including the area between the two nostrils. With the mouth and nose completed, the mixture is worked up toward the outer and upper jaw area, moving up and around the eyes to the forehead. The forehead area is covered completely back to the hair line and to the ear area. The eyes are the last area covered, with extreme care. The eyes are closed so foreign matter cannot get into them. Here there is an option, the eye area may be left open, carefully working around them taking care not to get anything in them, or, alternatively, the eyes are covered with a hard plastic cup-like device, the plastic cups then being covered with the alginate impression material. A third option is to cover the eye area just as the other areas of the face. (Since the eye area will be cut out of the finished product, it is being covered for convenience and safety rather than for the end result.)

The entire face or affected body area is covered with the alginate material, with the possible exception of the eyes, to an approximate thickness of between one-eighth (⅛) inch to one-quarter (¼) inch. It must be a solid cover; any holes or places left open during the covering process will leave an opening or a weakness in the impression. Strength and full coverage is important.

The second step in the masking process is actually performed simultaneously with the first or preceding step. While applying the alginate material, small strips of gauze are applied to the soft mixture. These gauze strips are cut from gauze pads and placed at hand while the alginate material is being applied. Before the alginate has hardened, and awhile it is on the face or body area, these strips are placed on the material. They are placed over the entire face or affected area so that they are exposed above the surface of the alginate material. When the alginate material is allowed to harden, most of the strip should be visible. The gauze is placed at random and over the entire face or body area. This stripping step is used to facilitate the bonding of the alginate impression material to a plaster material.

Plastering the Impression

With the gauze in place and the alginate material hardened, the impression is ready to be covered with a plaster material. The preferred plaster is in a powder form and must be mixed with water. This mixture is usually two (2) parts water to three (3) parts plaster, e.g. ninety-four (94) ml of water to one hundred (100) grams of powder. The first step is to mix equal parts of water and material in a clean plastic bowl, spatulating for fifteen (15) seconds. To this paint-like wash, the remaining part of powder is added gradually and spatulated thoroughly for fifteen (15) seconds with a rapid whipping stroke. This insures equal crystallization throughout the entire mass. Air bubbles are eliminated by rotating the bowl or patting or jarring its sides. Spatulation is continued rapidly until a thick creamy consistency is obtained. The plaster is now ready to apply over the alginate impression material. (It should be noted that the above proportions are approximate. As these materials absorb moisture from the air, slight variations in the proportions may be necessary. Furthermore, if the natural water has a high level of soluble salts, distilled water can be used.)

Once the plaster is mixed, as described above, it is applied over the alginate impression as soon as possible. It will begin to harden in a matter of a few seconds. The same methodology used to apply the alginate impression material can be used to apply the plaster. When practicing the facial mask embodiment of the invention, the process begins with the neck area. The plaster is worked up and around the chin and lower jaw, always with an upward stroke and making sure to cover the impression material completely. Moving up across the face, close attention is given the eye area, especially if the eyes areas were left uncovered. Complete coverage is again important. The nose area is vital to the strength of the plaster mold and complete coverage to that area is critical, but the nostrils are left open for breathing.

When practicing the facial mask embodiment of the invention, the entire face and neck area is covered with the plaster, leaving no area uncovered. Similarly, the entire body area to be treated should be covered with plaster. The alginate impression should not be visible at this point; it is covered completely.

Wrapping the Plaster

Before the plaster hardens, a plaster bandage wrap is used to cover the entire plastered area. The plaster bandage wrap is preferably three (3) inches wide by nine (9) feet long. While it remains rolled, the wrap is wetted thoroughly. The water is allowed to run between the edges of the wrap to assure that all areas of the bandage are wetted. The roll is pressed slightly until most of the excess water comes out, yet remaining thoroughly wet. In a progressive fashion, the bandage is unwrapped from its coiled posture and placed on the plastered face. Circular and back and forth motions are made around and across the face until the entire face is covered with the bandage. When practicing the facial mask embodiment of the invention, once the entire nine (9) feet of bandage is covering the face, the bandage is pressed down upon and rubbed in, smoothing it out over the entire surface of the face. Similar efforts area undertaken regarding bandages placed on body areas. Every attempt is made to make the plaster and the plaster bandage appear as one covering.

The bandage is applied to provide additional strength to the plaster and additional protection to the impression material during its removal from the face or body area. With the bandage securely in place, the plaster covering is allowed to harden. This could take from three (3) to ten (10) minutes depending on the temperature of the water used to wet the bandage, air temperature, and the thickness of the plaster. The plaster is inspected often, and as soon as it is hard enough to withstand removal, it is taken off.

Removing the Plastered Impression

When practicing the facial mask embodiment of the invention, as soon as the plaster is hard enough to hold the impression in place while it is being removed, the individual is raised to an upright position in the chair. The plaster is handled with both hands, one hand holding the plaster firmly under the neck area, while the other is over the front of the face area. The individual is asked to breathe through the mouth and blow the air out while making faces and moving the skin of the face as much as possible. While this is being done the impression with the plaster covering is slowly separated from the face. Special care is taken to make sure that no hair or skin is stuck to the impression material. The impression is lifted from the neck and chin out and upward, with the upper face and forehead being the last part of the face removed from the impression. Care is taken at all times during this process to make sure no damage is done to the alginate impression. When practicing the embodiment wherein the impression is made of a body area, the impression is carefully removed as well.

The removed, plaster-covered alginate impression comprises a negative image of the individual's face or body area from which a positive mold will be made. The impression is placed aside and the individuals face or body area is cleaned using the same type sterile eyelid cleanser that was used to clean the face or body area at the beginning of the process. The individual is not again needed until the fitting process.

Making the Mold

Once the negative image has been completed, the next step is to make a positive image (mold) from the plastered impression (negative image).

To begin this stage of the process, the negative image is placed in a secure position on a work area. It is positioned so that it will not move, leaving the open area (back of head in the facial mask embodiment) facing upward. The positive image or mold is made by filling the negative image with a hardening material. Preferably, the same plaster material used to form the cast over the impression material is used to fill the opening and form the mold.

The plaster material is mixed, as described in the previous section, and poured into the open area. The first bowl of mixed plaster, however, is mixed with less plaster powder to water ratio, causing it to be more liquid. This is done in order that the fresh plaster material will run into the many lines, wrinkles and other areas that require a more liquid matter for filling. The remainder of the bowls, usually four (4) total, are mixed at the same proportions as previously described. Beginning with the first bowl, the mixture is poured into the openings (back of head area in the facial mask embodiment) of the negative impression, and, with a stainless steel spatula, it is worked upward and outward, making sure it gets into every wrinkle, crevice and indentation in the alginate impression. Once the four (4) bowls have been mixed and poured into the impression, it is left to harden. It should harden in a matter of minutes, usually thirty (30) or less; however, if possible it is to be left longer to insure that it is hard enough to work with. Once the plaster material is hard, the impression material and the plaster covering is removed from the plaster mold. The plaster mold comprises a positive image of the individual's face or body area. The plaster covered aluminate impression is no longer needed.

The positive image (mold) must be a complete image of the individual's face or body area with no manufacturing blemishes. If there are holes or other areas of the mold that are not perfect, they can be repaired at this point. By mixing up a bowl of the plaster, using warm water for quick drying, the imperfections can be filled in and wet sanded to provide a more perfect mold. Once the positive image is in a usable condition, shaping begins.

Shaping the Mold

The subject is consulted to determine which area(s) of the face or body area needs the most attention, and that area of the mold is adjusted to specifications determined by the subject and the consultant. Adjustments are made by sculpting the mold in the areas of concentration. This sculpting is normally performed by cutting or grinding the mold at the appropriate sites. The work is preferably performed with a power grinder, either a grinder mounted on stationary platform or a hand held grinder. Different size bits may be used to shape the mold to specifications. This process is optional, however. Any method that adequately adjusts the contours of the mold is acceptable. For the process to be effective, the resulting mask should fit as tight as possible. The subject might find the mask to be a little uncomfortable at first, but as it begins to work the fit becomes more loose.

Once the mold has been shaped to the desired size, it is smoothed with a wet/dry sanding sponge to remove any irregular surface areas. The final step in making the mold ready for use is to hand smooth it. This process is accomplished by wetting the mold and using the hands to go over the entire surface of the mold to make it as smooth as possible. If any uneven surface appears that cannot be corrected by hand, one of the preceding steps may have to be redone. Once the mold is as smooth as possible, it is ready to be used to form the mask.

Forming the Mask From the Mold

The next procedure requires a larger work area. It also requires an oven, a perforated platform, a suction device for use underneath the perforated area, special non-sticking, flexible gloves that withstand heat up to 400° F., and a clear plastic sheet, preferably measuring approximately sixteen (16) inches by sixteen (16) inches. The plastic sheet will become the mask; therefore, it is very important to select it properly.

There are a number of plastic types that can be used. A clear nonporous plastic which allows for no bacterial build-up is preferred. By way of illustration, and not limitation, the following are known to be particularly useful in connection with the present invention:

(i) Polyethylene based plastic. This plastic provides good contact clarity, is safe, and offers a comfortable feel. It also has excellent hot strength, and is available in six (6) mm, nine (9) mm, and twelve (12) mm thicknesses.

(ii) An isonomer based plastic. This plastic has the same characteristics of polyethylene, except it is less rigid.

(iii) Modified polyethylene. This substance gives more support than polyethylene While retaining the same soft, comfortable feel, allowing the use of a thinner sheet to reduce bulk and weight while maintaining the desired support.

(iv) Clear co-polyester. This material is optically clear, providing superior viewing of underlying tissues and pressure points. It has been used for face masks on players in the NBA. It offers excellent thermoformability at a mulch lower temperature than most other plastics. It also can be modified with a heat gun after initial forming. Care must be taken with clear co-polyester not to overheat or brittleness may result. This plastic seems to be best suited to achieve the desired results.

The preferred mask is formed in accordance with the following procedures:

(1) The forming process begins with preheating the oven to 300° F. Higher temperatures may cause problems and are to be avoided.

(2) The positive mold is placed securely on the vacuum forming platform with the vacuum running and providing suction.

(3) The sheet of plastic is inserted into the oven and heated for about three (3) minutes or until it appears soft around the edges. Overheating may cause air bubbles or pockets. If this occurs the plastic sheet cannot be used, and another will have to be heated.

(4) Once the plastic is ready, it is removed from the oven by a handler using extreme caution and wearing the high temperature gloves.

(5) The plastic sheet is placed over the positive mold such that the droop of the sheet is pulled along the same direction as the pull from the vacuum.

(6) The sheet is pulled down over the positive mold until the plastic completely covers the mold as a second skin. The suction provides some help in pulling the soft plastic down over the mold, however, most of the pull and direction of the plastic comes from the hands pulling and stretching the plastic material over the mold. This process requires quickness and strength in the hands and arms as the plastic material will become hard in just ten (10) seconds. If the plastic is not covering the mold entirely within the first ten (10) seconds the plastic sheet is unusable and the process of forming the mask must begin again.

(7) The plastic sheet is left over the mold until it completely cools.

Certain preferred mold considerations function to insure the formation of an acceptable mask. These considerations are as follows:

(1) Use only a pure plaster mold, no additives or sealers should be used as the plastic may bond to these surfaces. Make sure that the positive mold is smooth and free of voids.

(2) Heating the mold lengthens the working time of the plastic material.

(3) Using a slightly wet, room temperature or warmer mold seems to work best. Dry molds should be moistened, while cold molds should be warmed to at least room temperature.

Completing the Mask

Once the plastic material has cooled, it is removed from the mold. Once removed from the mold, the excess plastic on the outer edges of the sheet is cut away with a cast cutting power saw. (The area of the plastic sheet that is to be removed will be turned up and away from the mold.) When practicing the facial mask embodiment of the invention, care is taken not to remove any part of the material touching the face area of the mold. Once the outer edges are cut assay, each eye area is measured and cut out with the same cast saw or similar jig-saw type instrument. The measurements for the eye cut-outs should be uniform and precise to assure the mask will have an even and uniform look. The mouth and nostrils are likewise measured and removed using the same instruments. Once the openings are cut and the outer edges are removed, a grinder is used to shape the openings and outer edges. A hand held instrument has more maneuverability and is preferred. The mask is held in the hand or in a vice while trimming and sanding/grinding the edges and openings. A knife is used to trim the excess rough plastic away from the edges once all the excess that can be removed by the grinder is taken off. All rough edges are then smoothed by first using a blade and file. The edges are filed to remove excess uneven areas. The smoother the edges, the easier the next step.

The final step in producing the mask is the rounding off of the edges. Once the rough areas are as smooth as they can get with the instruments used as described above, the edges are rounded off. This process involves heating the mask. In order to accomplish this a hand held torch is required, along with a small bowl of water. To begin the procedure, the portable heat torch (usually a butane powered heat source) is turned on. Once on, an area on the outer edge of the mask (about three (3) to four (4) inches) is heated for about ten (10) seconds. A "feel" for when the area is warm enough to work with will be acquired; however, the time required should be around ten (10) seconds. When the edges are warm the palm of the hand is used to glide or stroke the heated area in an outward and upward direction from the inside (closest to the face) to the outside. The fingers can be used in some areas, but the butt of the hand to the palm is best used to smooth out and round off the rough areas on the outer edges. Once the first three (3) to four (4) inch heated area is smoothed and rounded off, another area the same size is heated and the action, as described above, is repeated until the entire outside of the mask is smooth and no part of it is uncomfortable to the touch of the face.

Once the outer edge is smooth and there is no area on the edge that will be uncomfortable next to the face or body area, the same process is used to smooth and round off the eye, nose and mouth areas that have been cut open and smoothed with the knife and file in the facial mask embodiment of the invention. Because of the size of the openings, the fingers are used in these areas to smooth the openings instead of the palm of the hand. Again, the pressure strokes should be directed out and away from the side next to the face. This process is continued until all open areas are smooth and comfortable to the face. Once the masks has been made comfortable to the touch, and there are no rough areas, it is placed back on the mold. If there is any area of the mask that does not fit tightly to the mold, that area is heated and pressed down upon the mold until it fits against it. This is done to all areas of the mask that do not fit like a second skin to the mold. After the mask has been refitted to the mold, it is removed, cleaned and readied for fitting to the individual.

Fitting the Mask

The fitting process begins by placing the mask on the face or body area and checking for fit. If any area does not fit properly the mask is removed, the area heated, and adjustments are made to assure a better fit. The individual must communicate to the fitter how the mask fits, where it is too tight or too loose, and if any area is uncomfortable. All adjustments and refitting required is performed at this point. Once the fit is as near perfect as possible and no further adjustments are required, straps are put on the mask to hold it in place while it is being worn. These straps are preferably made of VELCRO, with positive and negative sides. The negative or "catch" side of the strap is placed on each side of the mask next to the outer edge, and two (2) positive straps are cut to go around the head or appropriate body area and catch the negative end.

The length of the straps will vary depending on the individual. When practicing the facial mask embodiment of the invention, it is important that they are long enough to go around the head and reach the strap catch on the other side of the mask. A third strap can be cut and used over the top of the head if desired. This will assist in pulling the mask in an upward direction.

Maintenance

During the first few times the mask is worn the individual may feel some uncomfortable areas, usually tightness, or the mask may need some other adjustment to insure a more proper fit. These adjustments are made in the manner described above. The mask is reheated and adjustments made to help cure the fitting problem.

After wearing the mask for a period of time, the subject may notice that the face begins to look thinner and the mask begins to fit more loose. When this happens the mask is again readjusted to fit the face in like manner. There is a limit, however, to the number and significance of adjustments that can be made to the mask. If the face requires a large amount of movement in the mask, a new mask may be necessary. If a new mask is required, the process begins anew.

The mask works to give support and pressure to troubled areas and may result in the reduction of the appearance of wrinkles, other blemishes caused by aged skin, unwanted mass or injury. It is theorized that the controlled directed pressure from the mask stimulates beneficial collagen production. The pressure is also thought to push the epidermis and dermis together so that, along with collagen production, separations between the two layers are minimized. The pressure also pushes scars or other skin irregularities down and promotes the growth of a uniform skin surface.

The subject may wear the mask around the house, the office, while working or driving, working in the yard, and during most daily activities. It is designed to be worn often and for an unlimited time. The time the mask is worn should be determined by the results desired. The results should be monitored and the wearing time adjusted accordingly.

In accordance with the aspect of the invention for shaping other areas of the body, such as the back, chest, arms and legs, the above described principles and methods may be utilized to treat various body areas of burn victims or others having severe scarring or skin irregularities.

Partial masks formed in accordance with the present invention for use in affecting other desired areas of the face or body are also contemplated in connection with the invention. The contour of the partial masks are formed and fitted from a sculpted positive mold as described above. The partial mask is then held in place using straps or alternate means.

This invention also encompasses the use of lotions, gels, burn dressings or other therapeutic substances placed under the mask to work in conjunction therewith. The invention might also be used in conjunction with laser surgeries to promote an enhanced appearance of lased body areas.

While the invention has been described with a certain degree of particularity, it is manifest that many changes may be made in the method hereinabove described without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method of manufacturing a body mask having a sculpted body contacting surface adapted to treat a subject's distinctive bodily characteristics, comprising:
   (a) forming a negative impression of the subject's targeted body area;
   (b) filling said impression with a hardening material;
   (c) when said hardening material has hardened, separating said impression from said hardening material, said hardening material being in the form of a mold reflecting a positive image of the body area;
   (d) sculpting said mold to achieve a desired body contacting surface; and
   (e) forming a mask for said mold.

2. The method of manufacturing a body mask according to claim 1, wherein step (a) further comprises covering the body area with an alginate impression material, applying gauze to said alginate impression material, covering said alginate impression material and gauze with a plaster material to form a plastered alginate impression of the body area, and removing said plaster alginate impression from the body area.

3. The method of manufacturing a body mask according to claim 1, wherein said mask is formed of plastic.

4. The method of manufacturing a body mask according to claim 3, wherein step (e) further comprises placing said mold securely on a vacuum forming platform, heating a plastic sheet and thereafter placing said plastic sheet over said mold, pulling said plastic sheet down over said mold to completely cover said mold, allowing said plastic sheet to cool, and removing excess material from said plastic sheet and rounding off and smoothing the edges and surfaces of said plastic sheet to obtain said mask.

5. The method of manufacturing a body mask according to claim 4, wherein said plastic sheet comprises a clear nonporous plastic.

6. A method of enhancing the appearance of a body area having wrinkles, blemishes or excess mass or having been disfigured by an injury such as a burn, said method comprising:
   (a) forming a body mask molded from a positive image of the subject's body area, the positive image having been sculpted to reflect the desired changes in the body area to be treated;
   (b) fitting said mask to the body area; and
   (c) applying said mask to the body for a time sufficient to enhance the appearance of the body area, refitting said mask as necessary.

7. The method of enhancing the appearance of a body area according to claim 6, wherein step (a) further comprises:
   (i) forming a negative impression of the subject's targeted body area;
   (ii) filling said impression with a hardening material;
   (iii) when said hardening material has hardened, separating said impression from said hardening material, said hardening material being in the form of a mold reflecting a positive image of the body area;
   (iv) sculpting said mold to achieve a desired body contacting surface; and
   (v) forming said mask from said mold.

8. The method of enhancing the appearance of a body area according to claim 7, wherein step (i) further comprises covering the body area with an alginate impression material, applying gauze to said alginate impression material, covering said alginate impression material and gauze with a plaster material to form a plastered alginate impression of the body area, and removing said plastered alginate impression from the body area.

9. The method of enhancing the appearance of a body area according to claim 7, wherein said mask is formed of plastic.

10. The method of enhancing the appearance of a body area according to claim 9, wherein step (v) further comprises placing said mold securely on a vacuum forming platform, heating a plastic sheet and thereafter placing said plastic sheet over said mold, pulling said plastic sheet down over said mold to completely cover said mold, allowing said plastic sheet to cool, and removing excess material from said plastic sheet and rounding off and smoothing the edges and surfaces of said plastic sheet to obtain said mask.

11. The method of enhancing the appearance of a body area according to claim 10, wherein said plastic sheet comprises a clear nonporous plastic.

12. A method of using a body mask to treat an injured or disfigured body area of a subject comprising:
   (a) fitting a body mask to the subject's body, such mask having a sculpted body contacting surface which applies a controlled and directed pressure against the injured or disfigured body area; and (b) applying said mask to the body for a time sufficient to promote growth of a uniform skin surface, refitting said mask as necessary.

13. The method of claim 12, wherein the body mask has been formed by:
   (i) forming a negative impression of the subject's targeted body area;
   (ii) filling said impression with a hardening material;
   (iii) when said hardening material has hardened, separating said impression from said hardening material, said hardening material being in the form of a mold reflecting a positive image of the body area;
   (iv) sculpting said mold to achieve a desired body contacting surface; and
   (v) forming a mask for said mold.

14. The method of claim 13, wherein step (i) further comprises covering the body area with an alginate impression material, applying gauze to said alginate impression material, covering said alginate impression material and gauze with a plaster material to form a plastered alginate impression of the body area, and removing said plaster alginate impression from the body area.

15. The method of claim 13, wherein said mask is formed of plastic.

16. The method of claim 15, wherein step (v) further comprises placing said mold securely on a vacuum forming platform, heating a plastic sheet and thereafter placing said plastic sheet over said mold, pulling said plastic sheet down over said mold to completely cover said mold, allowing said plastic sheet to cool, and removing excess material from said plastic sheet and rounding off and smoothing the edges and surfaces of said plastic sheet to obtain said mask.

17. The method of claim 16, wherein said plastic sheet comprises a clear nonporous plastic.

18. A shape-retaining body mask having a sculpted body contacting surface which mask has been manufactured by the following process:
   (a) forming a negative impression of the subject's targeted body area;
   (b) filling said impression with a hardening material;
   (c) when said hardening material has hardened, separating said impression from said hardening material, said hardening material being in the form of a mold reflecting a positive image of the body area;
   (d) sculpting said mold to achieve a desired body contacting surface; and
   (e) forming a mask which retains a shape registering with said mold.

19. The body mask of claim 18, wherein step (a) further comprises covering the body area with an alginate impression material, applying gauze to said alginate impression material, covering said alginate impression material and gauze with a plaster material to form a plastered alginate impression of the body area, and removing said plaster alginate impression from the body area.

20. The body mask of claim 18, wherein said mask is formed of plastic.

21. The body mask of claim 20, wherein step (e) further comprises placing said mold securely on a vacuum forming platform, heating a plastic sheet and thereafter placing said plastic sheet over said mold, pulling said plastic sheet down over said mold to completely cover said mold, allowing said plastic sheet to cool, and removing excess material from said plastic sheet and rounding off and smoothing the edges and surfaces of said plastic sheet to obtain said mask.

22. The body mask of claim 21, wherein said plastic sheet comprises a clear nonporous plastic.

* * * * *